US008282938B2

United States Patent
Uchida et al.

(10) Patent No.: US 8,282,938 B2
(45) Date of Patent: Oct. 9, 2012

(54) IMMUNOGENIC COMPOSITIONS COMPRISING LIPOSOMES AND AN INFLUENZA PB2 CTL EPITOPE OBTAINED FROM THE HIGHLY PATHOGENIC H5N1 STRAIN

(75) Inventors: Tetsuya Uchida, Tokyo (JP); Maiko Taneichi, Tokyo (JP); Kiichi Kajino, Sapporo (JP); Masanori Matsui, Saitama (JP); Hiroshi Oda, Kawasaki (JP)

(73) Assignees: National Institute of Infectious Diseases, Tokyo (JP); National University Corporation Hokkaido University, Sapporo-shi (JP); Saitama Medical University, Iruma-gun (JP); NOF Corporation, Tokyo (JP)

( * ) Notice: Subject to any disclaimer, the term of this patent is extended or adjusted under 35 U.S.C. 154(b) by 478 days.

(21) Appl. No.: 12/400,269

(22) Filed: Mar. 9, 2009

(65) Prior Publication Data

US 2010/0136098 A1  Jun. 3, 2010

(30) Foreign Application Priority Data

Nov. 28, 2008 (JP) ................................. 2008-303444

(51) Int. Cl.
*A61K 39/145* (2006.01)
*A61K 39/12* (2006.01)
*A61K 9/127* (2006.01)

(52) U.S. Cl. ................... 424/206.1; 424/450; 424/186.1
(58) Field of Classification Search .................... None
See application file for complete search history.

(56) References Cited

U.S. PATENT DOCUMENTS

| | | | |
|---|---|---|---|
| 4,789,633 A | 12/1988 | Huang et al. | |
| 2007/0055049 A1 | 3/2007 | Grey et al. | |
| 2008/0032921 A1 | 2/2008 | Alexander et al. | |
| 2008/0038329 A1 | 2/2008 | Uchida et al. | |
| 2008/0260762 A1 | 10/2008 | Grey et al. | |

FOREIGN PATENT DOCUMENTS

| | | |
|---|---|---|
| EP | 1 917 970 A2 | 5/2008 |
| JP | 2003-535024 A | 11/2003 |
| JP | 2008-037831 A | 2/2008 |
| WO | 2001/000225 A1 | 1/2001 |
| WO | 2008/039267 A2 | 4/2008 |
| WO | 2008/054540 A2 | 5/2008 |

OTHER PUBLICATIONS

Tetsuya, U., et al., 2008, T-cell activating agent, English translation of JP-A-2008-37831 (Feb. 21, 2008).*
Nagata, T., et al., 2007, Peptides coupled to the surface of a kind of liposome protect infection of influenza viruses, Vaccine 25:4914-4921.*
Wahl, A., et al., 2009, T-cell tolerance for variability in an HLA class I-presented influenza A virus epitope, J. Virol. 83(18):9206-9214.*
Hu, N., et al., 2005, Highly conserved pattern of recognition of influenza A wild-type and variant CD8+ CTL epitopes in HLA-A2+ humans and transgenic HLA-A2+/H2 class I-deficient mice, Vaccine 23:5231-5244.*
Rimmelzwaan, G. F., et al., 2009, Influenza virus CTL epitopes, remarkably conserved and remarkably variable, Vaccine 27:6363-6365.*
Rimmelzwaan, G. F., et al., 2004, Sequence variation in the influenza A virus nucleoprotein associated with escape from cytotoxic T lymphocytes, Vir. Res. 103:97-100.*
Heiny, A. T., et al., Nov. 2007, Evolutionarily conserved protein sequences of influenza A viruses, avian and human, as vaccine targets, PLoS ONE 2(11):e1190(1-14).*
Nagata et al., *Vaccine*, 25: 4914-4921 (2007).
Taneichi et al., *The Journal of Immunology*, 177: 2324-2330 (2006).
Uchida et al., *Mini-Reviews in Medicinal Chemistry*, 8: 184-192 (2008).
Uchida et al., *Bio Industry*, 25: 95-103 (2008).
Connor et al., *Proc. Natl. Acad. Sci.*, 81: 1715-1718 (Mar. 1984).
Hammond et al., *Proc. Natl. Acad. Sci.*, 102(18): 6320-6325 (May 3, 2005).
Lamb et al., *Journal of Virology*, 23(3): 816-819 (Sep. 1977).

* cited by examiner

*Primary Examiner* — Jeffrey S. Parkin
(74) *Attorney, Agent, or Firm* — Leydig, Voit & Mayer, Ltd.

(57) ABSTRACT

The present invention provides an avian influenza vaccine containing a peptide-bound liposome wherein; the peptide contains:
(1) an amino acid sequence shown by any one of SEQ ID NO:1 to 9, or
(2) an amino acid sequence shown by any one of SEQ ID NO:1 to 9
wherein one or two amino acids are substituted,
has a length of 9 to 11 amino acids, and
is capable of inducing HLA-restricted cytotoxic T lymphocytes;
wherein the liposome contains a phospholipid having an acyl group with 14 to 24 carbon atoms and one unsaturated bond or a hydrocarbon group with 14 to 24 carbon atoms and one unsaturated bond, and a liposome stabilizer; and
wherein the peptide is bound to the surface of the liposome.

17 Claims, No Drawings

SEQUENCE LISTING

```
<160> NUMBER OF SEQ ID NOS: 23

<210> SEQ ID NO 1
<211> LENGTH: 9
<212> TYPE: PRT
<213> ORGANISM: Highly-pathogenic avian influenza virus
      A/Hong_Kong/483/97(H5N1)

<400> SEQUENCE: 1

Gly Met Phe Asn Met Leu Ser Thr Val
1               5

<210> SEQ ID NO 2
<211> LENGTH: 9
<212> TYPE: PRT
<213> ORGANISM: Highly-pathogenic avian influenza virus
      A/Hong_Kong/483/97(H5N1)

<400> SEQUENCE: 2

Tyr Tyr Leu Glu Lys Ala Asn Lys Ile
1               5

<210> SEQ ID NO 3
<211> LENGTH: 9
<212> TYPE: PRT
<213> ORGANISM: Highly-pathogenic avian influenza virus
      A/Hong_Kong/483/97(H5N1)

<400> SEQUENCE: 3

Lys Thr Thr Pro Arg Pro Leu Arg Leu
1               5

<210> SEQ ID NO 4
<211> LENGTH: 9
<212> TYPE: PRT
<213> ORGANISM: Highly-pathogenic avian influenza virus
      A/Hong_Kong/483/97(H5N1)

<400> SEQUENCE: 4

Arg Tyr Thr Lys Thr Thr Tyr Trp Trp
1               5

<210> SEQ ID NO 5
<211> LENGTH: 9
<212> TYPE: PRT
<213> ORGANISM: Highly-pathogenic avian influenza virus
```

A/Hong_Kong/483/97(H5N1)

<400> SEQUENCE: 5

Ser Tyr Ile Asn Arg Thr Gly Thr Phe
1               5

<210> SEQ ID NO 6
<211> LENGTH: 9
<212> TYPE: PRT
<213> ORGANISM: Highly-pathogenic avian influenza virus
      A/Hong_Kong/483/97(H5N1)

<400> SEQUENCE: 6

Met Tyr Gln Lys Cys Cys Thr Leu Phe
1               5

<210> SEQ ID NO 7
<211> LENGTH: 9
<212> TYPE: PRT
<213> ORGANISM: Highly-pathogenic avian influenza virus
      A/Hong_Kong/483/97(H5N1)

<400> SEQUENCE: 7

Thr Tyr Gln Trp Ile Ile Arg Asn Trp
1               5

<210> SEQ ID NO 8
<211> LENGTH: 9
<212> TYPE: PRT
<213> ORGANISM: Highly-pathogenic avian influenza virus
      A/Hong_Kong/483/97(H5N1)

<400> SEQUENCE: 8

Ser Phe Ser Phe Gly Gly Phe Thr Phe
1               5

<210> SEQ ID NO 9
<211> LENGTH: 9
<212> TYPE: PRT
<213> ORGANISM: Highly-pathogenic avian influenza virus
      A/Hong_Kong/483/97(H5N1)

<400> SEQUENCE: 9

Ser Tyr Leu Ile Arg Ala Leu Thr Leu
1               5

<210> SEQ ID NO 10
<211> LENGTH: 9
<212> TYPE: PRT
<213> ORGANISM: Avian influenza virus A/PR8(H1N1)

<400> SEQUENCE: 10

Met Tyr Gln Arg Cys Cys Asn Leu Phe
1               5

<210> SEQ ID NO 11
<211> LENGTH: 9
<212> TYPE: PRT
<213> ORGANISM: Avian influenza virus A/Moscow(H3N2)

<400> SEQUENCE: 11

Lys Thr Thr Pro Arg Pro Ile Lys Leu
1               5

<210> SEQ ID NO 12
<211> LENGTH: 9

```
<212> TYPE: PRT
<213> ORGANISM: Avian influenza virus A/Moscow(H3N2)

<400> SEQUENCE: 12

Lys Tyr Thr Lys Thr Thr Tyr Trp Trp
1               5

<210> SEQ ID NO 13
<211> LENGTH: 9
<212> TYPE: PRT
<213> ORGANISM: Avian influenza virus A/Moscow(H3N2)

<400> SEQUENCE: 13

Ser Tyr Ile Asn Lys Thr Gly Thr Phe
1               5

<210> SEQ ID NO 14
<211> LENGTH: 9
<212> TYPE: PRT
<213> ORGANISM: Avian influenza virus A/Moscow(H3N2)

<400> SEQUENCE: 14

Met Tyr Gln Lys Cys Cys Asn Leu Phe
1               5

<210> SEQ ID NO 15
<211> LENGTH: 9
<212> TYPE: PRT
<213> ORGANISM: Avian influenza virus A/Moscow(H3N2)

<400> SEQUENCE: 15

Gly Tyr Leu Ile Arg Ala Leu Thr Leu
1               5

<210> SEQ ID NO 16
<211> LENGTH: 9
<212> TYPE: PRT
<213> ORGANISM: Highly-pathogenic avian influenza virus
        A/Hong_Kong/483/97(H5N1)

<400> SEQUENCE: 16

Leu Trp Ile Leu Asp Arg Leu Phe Phe
1               5

<210> SEQ ID NO 17
<211> LENGTH: 9
<212> TYPE: PRT
<213> ORGANISM: Highly-pathogenic avian influenza virus
        A/Hong_Kong/483/97(H5N1)

<400> SEQUENCE: 17

Thr Tyr Phe Glu Lys Val Glu Arg Leu
1               5

<210> SEQ ID NO 18
<211> LENGTH: 9
<212> TYPE: PRT
<213> ORGANISM: Highly-pathogenic avian influenza virus
        A/Hong_Kong/483/97(H5N1)

<400> SEQUENCE: 18

Glu Trp Phe Arg Asn Val Leu Ser Ile
1               5

<210> SEQ ID NO 19
<211> LENGTH: 9
```

-continued

```
<212> TYPE: PRT
<213> ORGANISM: Highly-pathogenic avian influenza virus
      A/Hong_Kong/483/97(H5N1)

<400> SEQUENCE: 19

Cys Phe Asn Pro Met Ile Val Glu Leu
1               5

<210> SEQ ID NO 20
<211> LENGTH: 9
<212> TYPE: PRT
<213> ORGANISM: Highly-pathogenic avian influenza virus
      A/Hong_Kong/483/97(H5N1)

<400> SEQUENCE: 20

Ile Phe Leu Ala Arg Ser Ala Leu Ile
1               5

<210> SEQ ID NO 21
<211> LENGTH: 9
<212> TYPE: PRT
<213> ORGANISM: Highly-pathogenic avian influenza virus
      A/Hong_Kong/483/97(H5N1)

<400> SEQUENCE: 21

Met Ser Asn Glu Gly Ser Tyr Phe Phe
1               5

<210> SEQ ID NO 22
<211> LENGTH: 9
<212> TYPE: PRT
<213> ORGANISM: Highly-pathogenic avian influenza virus
      A/Hong_Kong/483/97(H5N1)

<400> SEQUENCE: 22

Ser Leu Leu Thr Glu Val Glu Thr Leu
1               5

<210> SEQ ID NO 23
<211> LENGTH: 19
<212> TYPE: DNA
<213> ORGANISM: Artificial
<220> FEATURE:
<223> OTHER INFORMATION: Synthetic oligonucleotide

<400> SEQUENCE: 23
tccatgacgt tctgatgtt                                              19
```

US 8,282,938 B2

IMMUNOGENIC COMPOSITIONS COMPRISING LIPOSOMES AND AN INFLUENZA PB2 CTL EPITOPE OBTAINED FROM THE HIGHLY PATHOGENIC H5N1 STRAIN

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 4,667 bytes ASCII (Text) file named "704558 SequenceListing.txt," created Jun. 1, 2009.

CROSS-REFERENCES TO RELATED APPLICATIONS

This application is based on a patent application No. 2008-303444 filed in Japan (filing date: Nov. 28, 2008), the contents of which are incorporated in full herein by this reference.

TECHNICAL FIELD OF THE INVENTION

The present invention relates to peptides and peptide-bound liposomes that are useful for avian influenza vaccines, and uses thereof.

BACKGROUND OF THE INVENTION

Changing the surface antigenicity thereof by drifts, influenza viruses cause epidemics every year. Additionally, in a cycle of about 10 years to 40 years, new types of the viruses with antigenicity profiles totally different from those thereof have emerged as a result of shifts, which have caused worldwide extensive epidemics (hereinafter referred to as "pandemics") among the human beings, which lack immunity to the new types of the viruses.

Spanish flu, Hong Kong flu and other pandemics in the past are said to be likely to have been caused by avian influenza virus; an estimation is available that 5.00 million to 150.00 million people will possibly die of avian influenza in the future. Currently, infections with highly pathogenic avian influenza (H5N1), which produces high mortality rates, are reported around the world; effective countermeasures are urgently needed.

Generally, influenza viruses, including avian influenza virus, are likely to undergo mutations in the process of proliferation. Furthermore, if a virus that has infected to a human reasserts with human influenza virus in the body, a virus highly infectious among human beings possibly emerges while retaining the high pathogenicity. These frequent alterations of the viruses themselves are a reason for the repeated epidemics described above.

Point mutations (antigen drifts) occur in the genes that encode viral surface glycoproteins [hemagglutinin (HA) and neuraminidase (NA)], whereas antigen shifts produce novel strains with both genes altered immunologically.

Conventional vaccines induce the production of an antibody that binds specifically to a surface protein of influenza virus, and by means of the action of this antibody, deprive virus of the infectious potential. However, the surface proteins are likely to undergo mutations, as stated above, so that the antibodies induced by the above-described vaccines have not always been effective. At present, vaccines are reserved according to the type of virus expected to be prevalent, but the expectation is possibly a disappointment resulting in expanded damage.

Meanwhile, an internal protein of influenza virus is relatively highly conserved even in drift mutants and shift mutants; it is difficult to deactivate the protein by binding an antibody thereto from outside the virus, so that the internal protein has not been used proactively as a target for conventional vaccines.

Virus-infected cells expose on the surfaces thereof a major histocompatibility antigen complex (MHC) incorporating a portion of the amino acid sequence of a viral internal protein. If cytotoxic T lymphocytes capable of specifically killing virus-infected cells exhibiting these features could be prepared, it would be possible to effectively prevent the replication, and hence proliferation and spread of the virus, without being influenced by mutations.

JP-A-2008-37831 discloses a method of preparing a T cell activator capable of efficiently and specifically augmenting cytotoxic T lymphocytes (CD8$^+$ T cells, cytotoxic lymphocytes: CTL) for killing pathogen-infected cells or cancer cells using an antigen-bound liposome, and useful in the prevention or treatment of infectious diseases and cancers. However, it has been totally unclear whether the method can be actually effective in preventing infections with avian influenza virus, and what kind of antigen can be used to prepare effective cytotoxic T lymphocytes.

SUMMARY OF THE INVENTION

It is an object of the present invention to provide a vaccine for effectively preventing infections with highly pathogenic avian influenza virus, unlikely to be influenced by viral mutations.

The present inventors diligently investigated to accomplish the above-described object, and discovered an antigen epitope especially effective in preparing the above-described cytotoxic T lymphocytes, in a highly conserved internal protein sequence of highly pathogenic avian influenza virus. Furthermore, the present inventors found that by performing vaccination with a liposome with a peptide comprising this epitope bound thereto, antigen-specific cytotoxic T lymphocytes can be induced extremely potently, and developed the present invention.

Accordingly, the present invention is as follows.

[1] A peptide capable of inducing HLA-restricted cytotoxic T lymphocytes,
the peptide comprising:
(1) an amino acid sequence shown by any one of SEQ ID NO:1 to 9, or
(2) an amino acid sequence shown by any one of SEQ ID NO:1 to 9 wherein one or two amino acids are substituted, and having a length of 9 to 11 amino acids.

[2] The peptide according to [1], wherein the HLA is HLA-A*0201 or HLA-A*2402.

[3] A peptide-bound liposome; wherein
the peptide comprises:
(1) an amino acid sequence shown by any one of SEQ ID NO:1 to 9, or
(2) an amino acid sequence shown by any one of SEQ ID NO:1 to 9 wherein one or two amino acids are substituted, has a length of 9 to 11 amino acids, and
is capable of inducing HLA-restricted cytotoxic T lymphocytes; wherein the liposome comprises a phospholipid having an acyl group with 14 to 24 carbon atoms and one unsaturated bond or a hydrocarbon group with 14 to 24 carbon atoms and one unsaturated bond, and a liposome stabilizer; and wherein the peptide is bound to the surface of the liposome.

[4] The peptide-bound liposome according to [3], wherein the HLA is HLA-A*0201 or HLA-A*2402.

[5] The peptide-bound liposome according to [3], wherein the phospholipid is a phospholipid having an acyl group with 14 to 24 carbon atoms and one unsaturated bond.

[6] The peptide-bound liposome according to [3], wherein the acyl group is an oleoyl group.

[7] The peptide-bound liposome according to [3], wherein the phospholipid is at least one selected from among diacylphosphatidylserine, diacylphosphatidylglycerol, diacylphosphatidic acid, diacylphosphatidylcholine, diacylphosphatidylethanolamine, succinimidyl-diacylphosphatidylethanolamine, and maleimido-diacylphosphatidylethanolamine.

[8] The peptide-bound liposome according to [3], wherein the liposome stabilizer is cholesterol.

[9] The peptide-bound liposome according to [3], wherein the peptide is bound to a phospholipid having an acyl group with 14 to 24 carbon atoms and one unsaturated bond or a hydrocarbon group with 14 to 24 carbon atoms and one unsaturated bond, contained in a phospholipid membrane constituting the liposome.

[10] The peptide-bound liposome according to [3], wherein the liposome has the following composition:

(A) a phospholipid having an acyl group with 14 to 24 carbon atoms and one unsaturated bond or a hydrocarbon group with 14 to 24 carbon atoms and one unsaturated bond 1 to 99.8 mol %;

(B) a liposome stabilizer 0.2 to 75 mol %.

[11] The peptide-bound liposome according to [3], wherein the liposome has the following composition:

(I) an acidic phospholipid having an acyl group with 14 to 24 carbon atoms and one unsaturated bond or a hydrocarbon group with 14 to 24 carbon atoms and one unsaturated bond 1 to 85 mol %;

(II) a neutral phospholipid having an acyl group with 14 to 24 carbon atoms and one unsaturated bond or a hydrocarbon group with 14 to 24 carbon atoms and one unsaturated bond 0.01 to 80 mol %;

(III) a phospholipid having an acyl group with 14 to 24 carbon atoms and one unsaturated bond or a hydrocarbon group with 14 to 24 carbon atoms and one unsaturated bond, with a peptide bound thereto 0.2 to 80 mol %;

(IV) a liposome stabilizer 0.2 to 75 mol %.

[12] A cytotoxic T lymphocyte activator comprising a peptide, wherein the peptide comprises:

(1) an amino acid sequence shown by any one of SEQ ID NO:1 to 9, or (2) an amino acid sequence shown by any one of SEQ ID NO:1 to 9 wherein one or two amino acids are substituted, has a length of 9 to 11 amino acids, and is capable of inducing HLA-restricted cytotoxic T lymphocytes.

[13] A cytotoxic T lymphocyte activator comprising the peptide-bound liposome according to [3].

[14] The cytotoxic T lymphocyte activator according to [12], further comprising CpG-DNA.

[15] The cytotoxic T lymphocyte activator according to [13], further comprising CpG-DNA.

[16] An avian influenza virus vaccine comprising a peptide, wherein the peptide comprises:

(1) an amino acid sequence shown by any one of SEQ ID NO:1 to 9, or (2) an amino acid sequence shown by any one of SEQ ID NO:1 to 9 wherein one or two amino acids are substituted, has a length of 9 to 11 amino acids, and is capable of inducing HLA-restricted cytotoxic T lymphocytes.

[17] An avian influenza virus vaccine comprising the peptide-bound liposome according to [3].

[18] The avian influenza virus vaccine according to [16], further comprising CpG-DNA.

[19] The avian influenza virus vaccine according to [17], further comprising CpG-DNA.

[20] A method of activating cytotoxic T lymphocytes in a mammal, comprising administering to the mammal a peptide that comprises:

(1) an amino acid sequence shown by any one of SEQ ID NO:1 to 9, or (2) an amino acid sequence shown by any one of SEQ ID NO:1 to 9 wherein one or two amino acids are substituted, has a length of 9 to 11 amino acids, and is capable of inducing HLA-restricted cytotoxic T lymphocytes.

[21] A method of activating cytotoxic T lymphocytes in a mammal, comprising administering to the mammal the peptide-bound liposome according to [3].

[22] The method according to [20], further comprising administering CpG-DNA.

[23] The method according to [21], further comprising administering CpG-DNA.

[24] A method of vaccinating a mammal against avian influenza virus, comprising administering to the mammal a peptide that comprises, (1) an amino acid sequence shown by any one of SEQ ID NO:1 to 9, or (2) an amino acid sequence shown by any one of SEQ ID NO:1 to 9 wherein one or two amino acids are substituted, has a length of 9 to 11 amino acids, and is capable of inducing HLA-restricted cytotoxic T lymphocytes.

[25] A method of vaccinating a mammal against avian influenza virus, comprising administering the peptide-bound liposome according to [3] to the mammal.

[26] The method according to [24], further comprising administering CpG-DNA.

[27] The method according to [25], further comprising administering CpG-DNA.

Using the peptide and peptide-bound liposome of the present invention, an avian influenza vaccine can be prepared from an antigen derived from a highly conserved internal protein of avian influenza virus. According to the present invention, it is possible to provide a highly versatile avian influenza vaccine, different from conventional avian influenza vaccines, that is unlikely to be influenced by viral surface protein mutations to obviate the need for the accurate estimation of the virus strain (type or subtype) expected to become prevalent.

DETAILED DESCRIPTION OF THE INVENTION

The present invention provides a peptide capable of inducing HLA-restricted cytotoxic T lymphocytes, comprising (1) an amino acid sequence shown by any one of SEQ ID NO:1 to 9, or (2) an amino acid sequence shown by any one of SEQ ID NO:1 to 9 wherein one or two amino acids are substituted, and having a length of 9 to 11 amino acids (the peptide of the present invention).

The present invention has been developed on the basis of the discovery of the following excellent epitope sequences (the epitope sequences of the present invention) in highly pathogenic avian influenza virus antigens:

amino acid sequences shown by any one of SEQ ID NO:1 to 9 amino acid sequences shown by any one of SEQ ID NO:1 to 9 wherein one or two amino acids are substituted (here, a peptide consisting of the amino acid sequence is capable of inducing HLA-restricted cytotoxic T lymphocytes).

An amino acid sequence shown by SEQ ID NO:1 to 9 corresponds to a partial sequence present in the amino acid sequences of the internal proteins PA (SEQ ID NO:2 and 3), PB1 (SEQ ID NO:1, 4, 5, 6 and 9) and PB2 (SEQ ID NO:7 and 8) of the highly pathogenic avian influenza virus A/Hong_Kong/483/97(H5N1).

The mode of the substitution in (2) is not particularly limited, as far as the peptide consisting of the amino acid sequence is capable of inducing HLA-restricted cytotoxic T lymphocytes; one reflecting a known amino acid mutation that has occurred in a corresponding epitope sequence in the same antigen of a different avian influenza virus strain (type or subtype) can be mentioned as a preferred mode. As examples of such substitutions, the following can be mentioned.

```
MYQKCCTLF (SEQ ID NO: 6)  → MYQRCCNLF (SEQ ID NO: 10) PR8 (H1N1)

KTTPRPLRL (SEQ ID NO: 3)  → KTTPRPIKL (SEQ ID NO: 11) Moscow (H3N2)

RYTKTTYWW (SEQ ID NO: 4)  → KYTKTTYWW (SEQ ID NO: 12) Moscow (H3N2)

SYINRTGTF (SEQ ID NO: 5)  → SYINKTGTF (SEQ ID NO: 13) Moscow (H3N2)

MYQKCCTLF (SEQ ID NO: 6)  → MYQKCCNLF (SEQ ID NO: 14) Moscow (H3N2)

SYLIRALTL (SEQ ID NO: 9)  → GYLIRALTL (SEQ ID NO: 15) Moscow (H3N2)
```

The epitope sequence of the present invention and a peptide consisting of the sequence (the epitope peptide of the present invention) have the following excellent characteristics:

(A) The epitope of the present invention is highly conserved in drift mutants and shift mutants of avian influenza virus.

(B) The epitope peptide of the present invention is stably presented onto human major histocompatibility antigen (HLA). Although the type of HLA is not particularly limited, the epitope peptide of the present invention is particularly excellent in the bindability to HLA-A*0201 and HLA-A*2402, the most common types of HLA in the world.

(C) Having the characteristic (B), the epitope peptide of the present invention is capable of potently inducing HLA (preferably HLA-A*0201 or HLA-A*2402)-restricted cytotoxic T lymphocytes. "An antigen induces HLA-restricted cytotoxic T lymphocytes" means that when a mammal (for example, humans, transgenic mice and the like) expressing a particular HLA (for example, HLA-A*0201 or HLA-A*2402) is immunized with an antigen, the number and/or activity (for example, cytotoxic activity) of cytotoxic T lymphocytes that are restricted to the HLA and specifically recognize the antigen rises in the body of the mammal. Because HLA-A*0201 and HLA-A*2402 are the most common of its kind in the world, as stated above, the epitope peptide of the present invention is capable of inducing cytotoxic T lymphocytes in the human beings all over the world, irrespective of racial differences, to activate cellular immunity. From the viewpoints described above, epitopes of HLA-A*0201-restricted PB1_410: GMFN-MLSTV (SEQ ID NO:1) and HLA-A*2402-restricted PA_130: YYLEKANKI (SEQ ID NO:2), PA_262: KTTPRPLRL (SEQ ID NO:3), PB1_430: RYTKTTYWW (SEQ ID NO:4), PB1_482: SYINRTGTF (SEQ ID NO:5), PB1_688: MYQKCCTLF (SEQ ID NO:6) and PB2_549: TYQWIIRNW (SEQ ID NO:7) are preferable, and PB1_410: GMFNMLSTV (SEQ ID NO:1), PA_130: YYLEKANKI (SEQ ID NO:2), PB1_430: RYTKTTYWW (SEQ ID NO:4), PB1_688: MYQKCCTLF (SEQ ID NO:6) and PB2_549: TYQWIIRNW (SEQ ID NO:7) are particularly preferable.

The peptide of the present invention is the above-described epitope peptide of the present invention as it is, or undergoes cleavage by the action of proteasome and the like in cells to produce the above-described epitope peptide of the present invention. Therefore, the peptide of the present invention possesses substantially the same excellent characteristics as those of the epitope peptide of the present invention; when used for producing the cytotoxic T lymphocyte activator and avian influenza virus vaccine of the present invention as described below, the peptide of the present invention exhibits excellent effects in killing the cells infected with avian influenza virus and preventing infections with avian influenza virus.

The length of the peptide of the present invention is not particularly limited, and is normally 9 to 11 amino acids, preferably 9 to 10 amino acids, and more preferably 9 amino acids. When the length of the peptide of the present invention is 10 amino acids or more, the peptide of the present invention has an additional sequence on the N-terminal side and/or C-terminal side of the epitope sequence of the present invention. The length and amino acid sequence of the additional sequence is not particularly limited, as far as the above-described characteristics of the peptide of the present invention are not affected. For example, the additional sequence can be an amino acid sequence actually existing adjacent to a partial sequence corresponding to any one of SEQ ID NO:1 to 9 in the amino acid sequences of the PA, PB1 and PB2 proteins of an avian influenza virus (for example, highly pathogenic avian influenza virus A/Hong_Kong/483/97 (H5N1)). Particularly preferred is a residue capable of overcoming the selection of an antigen to be presented, due to personal differences in MHC (polymorphism) when the above-described peptide forms a major histocompatibility antigen complex (MHC) in cells.

In a preferred mode, the peptide of the present invention comprises a plurality of kinds (for example, 2 to 9 kinds, preferably 5 to 9 kinds) of the above-described epitope sequence of the present invention. A number and combination of kinds of epitope sequences can be set optionally. Because a plurality of the epitope sequences of the present invention are included in the peptide of the present invention, as described above, the potential of the peptide of the present invention for inducing cytotoxic T lymphocytes increases; when the peptide of the present invention as such is used for producing an avian influenza virus vaccine, the preventive effect against avian influenza virus infection can be improved dramatically.

The peptide of the present invention can be prepared by, for example, a known technique for peptide synthesis, such as liquid phase synthesis or solid phase peptide synthesis. Alternatively, a transformant (Escherichia coli and the like) incorporating an expression vector capable of expressing the peptide of the present invention is cultured, and the peptide of the present invention is isolated from the culture by a commonly known technique for purification such as an affinity column, whereby the peptide of the present invention can be produced. An expression vector capable of expressing the peptide of the present invention can be constructed by ligating a polynucleotide that encodes the peptide of the present invention downstream of a promoter in an appropriate expression vector using a commonly known technique for gene engineering.

The present invention also provides a peptide-bound liposome being a liposome with the above-described peptide of the present invention bound thereto, wherein
the liposome comprises a phospholipid having an acyl group with 14 to 24 carbon atoms and one unsaturated bond or a hydrocarbon group with 14 to 24 carbon atoms and one unsaturated bond, and a liposome stabilizer; and
wherein the above-described peptide of the present invention is bound to the surface of the liposome (the peptide-bound liposome of the present invention).

The phospholipid membrane constituting the liposome moiety of the peptide-bound liposome of the present invention has a structure wherein a phospholipid, which is an amphoteric surfactant, forms an interface with the polar group thereof facing the water phase side, and the hydrophobic group thereof facing the opposite side of the interface. Here, a liposome refers to a phospholipid double membrane having a closed space.

The peptide of the present invention is capable of binding to the surface of a liposome via a functional group possessed thereby. As functional groups in the peptide of the present invention used for binding to the surface of a liposome, an amino group, a thiol group, a carboxyl group, a hydroxy group, a disulfide group, a hydrophobic group consisting of a hydrocarbon group (alkyl group and the like) having a methylene chain, and the like can be mentioned. These groups are capable of allowing the peptide of the present invention to bind to the surface of a liposome, by a covalent bond for an amino group, a thiol group, a carboxyl group, a hydroxy group and a disulfide group, by an ionic bond for an amino group and a carboxyl group, and by a hydrophobic bond between hydrophobic groups. The peptide of the present invention binds to the surface of a liposome preferably via an amino group, a carboxyl group or a thiol group.

It is desirable that the phospholipid membrane constituting the liposome have a functional group such as an amino group, a succinimide group, a maleimide group, a thiol group, a carboxyl group, a hydroxy group, a disulfide group, or a hydrophobic group consisting of a hydrocarbon group (alkyl group and the like) having a methylene chain, so that the peptide of the present invention may stably bind to a liposome via a functional group possessed by the peptide of the present invention. The functional group possessed by the phospholipid membrane constituting the liposome is preferably an amino group, a succinimide group or a maleimide group. A combination of a functional group possessed by the peptide of the present invention and a functional group possessed by the phospholipid membrane constituting the liposome, involved in the binding of the peptide of the present invention to the liposome, can be optionally chosen, as far as the effect of the present invention is not influenced; as preferable combinations, an amino group and an aldehyde group, an amino group and an amino group, an amino group and a succinimide group, a thiol group and a maleimide group and the like can be mentioned. Ionic bonds and hydrophobic bonds are preferable from the viewpoint of the ease of preparation of a peptide-bound liposome because of the convenient procedure of binding of the peptide to the liposome, and covalent bonds are preferable in view of the binding stability of the peptide of the present invention on the liposome surface or storage stability in practical use of the peptide-bound liposome. A feature of the peptide-bound liposome of the present invention resides in the fact that the peptide of the present invention is bound to the surface of the liposome being a constituent thereof, whereby an excellent cytotoxic T lymphocyte activating effect is achieved. Therefore, in practical settings, it is preferable in view of enhancement of the effect of the present invention that, even after being administered to a living organism by the act of injection, for example, the peptide of the present invention be stably bound to the surface of the liposome. From this viewpoint, the bond between the peptide of the present invention and the liposome is preferably a covalent bond.

The phospholipid membrane constituting the liposome moiety of the peptide-bound liposome of the present invention comprises a phospholipid having an acyl group with 14 to 24 carbon atoms and one unsaturated bond or a hydrocarbon group with 14 to 24 carbon atoms and one unsaturated bond, and a liposome stabilizer.

In the phospholipid having an acyl group with 14 to 24 carbon atoms and one unsaturated bond, the number of carbon atoms of the acyl group is preferably 16 to 22, more preferably 18 to 22, and most preferably 18. As the acyl group, specifically, a palmitoleoyl group, an oleoyl group, an erucoyl group and the like can be mentioned, and an oleoyl group is most preferable.

In the phospholipid having a hydrocarbon group with 14 to 24 carbon atoms and one unsaturated bond, the number of carbon atoms of the hydrocarbon group is preferably 16 to 22, more preferably 18 to 22, and most preferably 18. As the hydrocarbon group specifically, a tetradecenyl group, a hexadecenyl group, an octadecenyl group, a C20 monoene group, a C22 monoene group, a C24 monoene group and the like can be mentioned.

The unsaturated acyl groups or unsaturated hydrocarbon groups that bind to the 1-position and 2-position of the glycerin residue present in the phospholipid may be identical or different. From the viewpoint of industrial productivity, it is preferable that the groups at the 1-position and 2-position be identical.

As the phospholipid, a phospholipid having an acyl group with 14 to 24 carbon atoms and one unsaturated bond is preferably used.

It is an object of the present invention to efficiently and specifically augment cytotoxic T lymphocytes (CD8$^+$ T cells, CTL) for killing cells infected with avian influenza virus. In view of enhancement of CTL activity to a practically sufficient level, it is preferable that the phospholipid have an acyl group with 14 to 24 carbon atoms and one unsaturated bond. If the number of carbon atoms of the acyl group is less than 13, the liposome stability worsens, or the CTL activity enhancing effect is insufficient in some cases. If the number of carbon atoms of the acyl group exceeds 24, the liposome stability worsens in some cases.

As the phospholipid having an acyl group with 14 to 24 carbon atoms and one unsaturated bond or a hydrocarbon group with 14 to 24 carbon atoms and one unsaturated bond, an acidic phospholipid, a neutral phospholipid, a reactive phospholipid having a functional group capable of binding a peptide and other kinds can be mentioned. These can be chosen as appropriate with respect to the kind and ratio thereof according to various requirements.

As the acidic phospholipid, phosphatidylserine, phosphatidylglycerol, phosphatidic acid, phosphatidylinositol and the like can be used. In view of enhancement of CTL activity to a practically sufficient level, and industrial supply, quality for pharmaceutical use and the like, diacylphosphatidylserine, diacylphosphatidylglycerol, diacylphosphatidic acid, and diacylphosphatidylinositol having an acyl group with 14 to 24 carbon atoms and one unsaturated bond are preferably used. An acidic phospholipid confers an anionic ionized group to the surface of a liposome, thus conferring a negative zeta potential to the liposome surface. For this reason, the liposome acquires a charge-based repulsive force, and can exist as a stable preparation in an aqueous solvent. Hence, an acidic phospholipid is important in assuring liposome stability when the peptide-bound liposome of the present invention is present in an aqueous solvent.

As the neutral phospholipid, for example, phosphatidylcholine and the like can be used. A neutral phospholipid that can be used in the present invention, as far enhancement of CTL activity, an object of the present invention, is accomplished, can be chosen as appropriate with respect to the kind and amount thereof. A neutral phospholipid, compared with an acidic phospholipid and a phospholipid with the peptide of the present invention bound thereto, is more highly functional in stabilizing liposomes, thus being capable of improving membrane stability. From this viewpoint, it is preferable that the phospholipid membrane constituting the liposome moiety of the peptide-bound liposome of the present invention comprise a neutral phospholipid. Provided that sufficient contents of an acidic phospholipid used to achieve a CTL activity enhancing effect, a reactive phospholipid for peptide binding and a liposome stabilizer are assured, the amount of neutral phospholipid used can be determined.

In the peptide-bound liposome of the present invention, the peptide of the present invention binds to the surface of the liposome by binding to a phospholipid having an acyl group with 14 to 24 carbon atoms and one unsaturated bond or a hydrocarbon group with 14 to 24 carbon atoms and one unsaturated bond, contained in the phospholipid membrane constituting the liposome.

As a phospholipid for this peptide binding, a reactive phospholipid having a functional group capable of having the peptide of the present invention bound thereto is used. A reactive phospholipid having an acyl group with 14 to 24 carbon atoms and one unsaturated bond or a hydrocarbon group with 14 to 24 carbon atoms and one unsaturated bond can be chosen as appropriate with respect to the kind and ratio thereof according to various requirements. As with the above-described phospholipids, for the reactive phospholipid, it is undesirable that the number of carbon atoms of the unsaturated acyl group or unsaturated hydrocarbon group contained in the phospholipid exceeds 24 or is less than 14.

As the reactive phospholipid, phosphatidylethanolamine or a terminal-modified derivative thereof can be mentioned. Phosphatidylglycerol, phosphatidylserine, phosphatidic acid, phosphatidylinositol and terminal-modified derivatives thereof can also be used as the reactive phospholipid. From the viewpoints of industrial availability, the simplicity of the step of binding to the peptide of the present invention, percent yield and the like, it is preferable that phosphatidylethanolamine or a terminal-modified derivative thereof be used. Phosphatidylethanolamine has an amino group capable of having the peptide of the present invention bound to an end thereof. Furthermore, in view of enhancement of CTL activity to a practically sufficient level, stability in liposomes, industrial supply, quality for pharmaceutical use and the like, diacylphosphatidylethanolamine having an acyl group with 14 to 24 carbon atoms and one unsaturated bond, or a terminal-modified derivative thereof is most preferably used.

Diacylphosphatidylethanolamine can be obtained by, for example, carrying out a base exchange reaction of choline and ethanolamine using phospholipase D, with diacylphosphatidylcholine as a raw material. Specifically, a chloroform solution of diacylphosphatidylcholine, and water with phospholipase D and ethanolamine dissolved therein are mixed in an appropriate ratio, whereby a crude reaction product can be obtained. The crude reaction product is purified using a chloroform/methanol/aqueous solvent in a silica gel column, whereby the desired diacylphosphatidylethanolamine can be obtained. Those skilled in the art are able to carry out this process using appropriately chosen column purification conditions such as solvent composition ratio.

As a terminal-modified derivative, a diacylphosphatidylethanolamine terminal-modified derivative prepared by binding one end of a divalent reactive compound to the amino group of diacylphosphatidylethanolamine can be mentioned. As the divalent reactive compound, a compound having at least one end thereof an aldehyde group or succinic imide group capable of reacting with the amino group of diacylphosphatidylethanolamine can be utilized. As divalent reactive compounds having an aldehyde group, glyoxal, glutaraldehyde, succinedialdehyde, terephthalaldehyde and the like can be mentioned. Preferably, glutaraldehyde can be mentioned. As divalent reactive compounds having a succinic imide group, dithiobis(succinimidyl propionate), ethylene glycol-bis(succinimidyl succinate), disuccinimidyl succinate, disuccinimidyl suberate, disuccinimidyl glutarate and the like can be mentioned.

As divalent reactive compounds having a succinimide group at one end thereof and a maleimide group at the other end, N-succinimidyl 4-(p-maleimidophenyl)butyrate, sulfosuccinimidyl-4-(p-maleimidophenyl)butyrate, N-succinimidyl-4-(p-maleimidophenyl)acetate, N-succinimidyl-4-(p-maleimidophenyl)propionate, succinimidyl-4-(N-maleimidethyl)-cyclohexane-1-carboxylate, sulfosuccinimidyl-4-(N-maleimidethyl)-cyclohexane-1-carboxylate, N-(γ-maleimidobutyryloxy)succinimide, N-(ε-maleimidocaproyloxy)succinimide and the like can be mentioned. Using these divalent reactive compounds, a diacylphosphatidylethanolamine terminal-modified derivative having a maleimide group as a functional group can be obtained. The functional group at one end of a divalent reactive compound as described above is bound to the amino group of diacylphosphatidylethanolamine, whereby a diacylphosphatidylethanolamine terminal-modified derivative can be obtained.

As an example of a method of binding the peptide of the present invention to the surface of a liposome, a method can be mentioned wherein a liposome comprising one of the above-described reactive phospholipids is prepared, and then the peptide of the present invention is added to bind the peptide to the reactive phospholipid in the liposome. Also by binding the peptide of the present invention to a reactive phospholipid in advance, and then mixing the thus-obtained reactive phospholipid having the peptide of the present invention bound thereto with a phospholipid other than the reactive phospholipid and a liposome stabilizer, a liposome having the peptide of the present invention bound to the surface thereof can be obtained. A method of binding the peptide of the present invention to a reactive phospholipid is well known in the art.

The phospholipid membrane constituting the liposome moiety of the peptide-bound liposome of the present invention comprises at least 1 kind, for example, 2 kinds or more, preferably 3 kinds or more, of phospholipids having an acyl group with 14 to 24 carbon atoms and one unsaturated bond or a hydrocarbon group with 14 to 24 carbon atoms and one unsaturated bond.

For example, the phospholipid membrane constituting the liposome moiety of the peptide-bound liposome of the present invention comprises at least 1 kind, for example, 2 kinds or more, preferably 3 kinds or more, of phospholipids having an acyl group with 14 to 24 carbon atoms and one unsaturated bond or a hydrocarbon group with 14 to 24 carbon atoms and one unsaturated bond, selected from among diacylphosphatidylserine, diacylphosphatidylglycerol, diacylphosphatidic acid, diacylphosphatidylcholine, diacylphosphatidylethanolamine, succinimidyl-diacylphosphatidylethanolamine, and maleimido-diacylphosphatidylethanolamine.

The phospholipid membrane constituting the liposome moiety of the peptide-bound liposome of the present invention preferably comprises at least 1 kind of each of:
an acidic phospholipid having an acyl group with 14 to 24 carbon atoms and one unsaturated bond or a hydrocarbon group with 14 to 24 carbon atoms and one unsaturated bond,
a neutral phospholipid having an acyl group with 14 to 24 carbon atoms and one unsaturated bond or a hydrocarbon group with 14 to 24 carbon atoms and one unsaturated bond, and
a reactive phospholipid having an acyl group with 14 to 24 carbon atoms and one unsaturated bond or a hydrocarbon group with 14 to 24 carbon atoms and one unsaturated bond.

In the present invention, as a liposome stabilizer, sterols or tocopherols can be used. The sterols may be those generally known as sterols; for example, cholesterol, sitosterol, campesterol, stigmasterol, brassica sterol and the like can be mentioned; in view of availability and the like, cholesterol is used particularly preferably. The above-described tocopherols may be those generally known as tocopherols; for example, in view of availability and the like, commercially available α-tocopherol is preferably mentioned.

Furthermore, as far as the effect of the present invention is not affected, the phospholipid membrane constituting the liposome moiety of the peptide-bound liposome of the present invention may comprise a publicly known constituent capable of constituting a liposome.

As an example of the composition of the phospholipid membrane constituting the liposome moiety of the peptide-bound liposome of the present invention, the following can be mentioned:
(A) a phospholipid having an acyl group with 14 to 24 carbon atoms and one unsaturated bond or a hydrocarbon group with 14 to 24 carbon atoms and one unsaturated bond 1 to 99.8 mol %;
(B) a liposome stabilizer 0.2 to 75 mol %

The content of each component is indicated as mol % to all components of the phospholipid membrane constituting the liposome moiety of the peptide-bound liposome.

The content of the above-described component (A) is, from the viewpoint of liposome stability, preferably 10 to 90 mol %, more preferably 30 to 80 mol %, and still more preferably 50 to 70 mol %.

The content of the above-described component (B) is, from the viewpoint of liposome stability, preferably 5 to 70 mol %, more preferably 10 to 60 mol %, and still more preferably 20 to 50 mol %. If the content of the stabilizer exceeds 75 mol %, the liposome stability is affected, and this is undesirable.

The above-described component (A) includes the following:
(a) a phospholipid having an acyl group with 14 to 24 carbon atoms and one unsaturated bond or a hydrocarbon group with 14 to 24 carbon atoms and one unsaturated bond, to which the peptide of the present invention is not bound, and
(b) a phospholipid having an acyl group with 14 to 24 carbon atoms and one unsaturated bond or a hydrocarbon group with 14 to 24 carbon atoms and one unsaturated bond, to which the peptide of the present invention is bound.

The content of the above-described component (a) is normally 0.01 to 85 mol %, preferably 0.1 to 80 mol %, more preferably 0.1 to 60 mol %, still more preferably 0.1 to 50 mol %.

The content of the above-described component (b) is normally 0.2 to 80 mol %, preferably 0.3 to 60 mol %, more preferably 0.4 to 50 mol %, and still more preferably 0.5 to 25 mol %. If the content is less than 0.2 mol %, the amount of the peptide of the present invention decreases, so that it becomes difficult to activate cytotoxic T lymphocytes to a practically sufficient level; if the content exceeds 80 mol %, liposome stability decreases.

The phospholipid of the above-described component (a) normally includes the above-described acidic phospholipid and neutral phospholipid. The phospholipid of the above-described component (b) includes the above-described reactive phospholipid.

The content of the acidic phospholipid is normally 1 to 85 mol %, preferably 2 to 80 mol %, more preferably 4 to 60 mol %, and still more preferably 5 to 40 mol %. If the content is less than 1 mol %, the zeta potential decreases and the liposome stability lowers, and it becomes difficult to activate cytotoxic T lymphocytes to a practically sufficient level. Meanwhile, if the content exceeds 85 mol %, the content of the phospholipid with the peptide of the present invention bound thereto in the liposome decreases, making it difficult to activate cytotoxic T lymphocytes to a practically sufficient level.

The content of the neutral phospholipid is normally 0.01 to 80 mol %, preferably 0.1 to 70 mol %, more preferably 0.1 to 60 mol %, and still more preferably 0.1 to 50 mol %. If the content exceeds 80.0 mol %, the contents of the acidic phospholipid, the phospholipid with the peptide of the present invention bound thereto and the liposome stabilizer in the liposome decrease, so that it becomes difficult to activate cytotoxic T lymphocytes to a practically sufficient level.

A phospholipid with the peptide of the present invention bound thereto is obtained by binding the peptide of the present invention to the reactive phospholipid described above; the ratio of the reactive phospholipid bound to the peptide of the present invention can be chosen as appropriate, as far as the effect of the present invention is not interfered with, according to the kind of functional group used for the binding, binding treatment conditions employed and the like.

For example, when a terminal-modified derivative of diacylphosphatidylethanolamine obtained by binding one end of disuccinimidyl succinate, a divalent reactive compound, to the terminal amino group of diacylphosphatidylethanolamine, is used as the reactive phospholipid, it is possible to bind 10 to 99% of the reactive phospholipid to the peptide of the present invention by choosing binding treatment conditions. In this case, the reactive phospholipid not bound to the peptide of the present invention becomes an acidic phospholipid and gets contained in the liposome.

As a preferred mode of the phospholipid membrane constituting the liposome moiety of the peptide-bound liposome of the present invention, the following composition can be mentioned:
(I) an acidic phospholipid having an acyl group with 14 to 24 carbon atoms and one unsaturated bond or a hydrocarbon group with 14 to 24 carbon atoms and one unsaturated bond 1 to 85 mol %;
(II) a neutral phospholipid having an acyl group with 14 to 24 carbon atoms and one unsaturated bond or a hydrocarbon group with 14 to 24 carbon atoms and one unsaturated bond 0.01 to 80 mol %;
(III) a phospholipid having an acyl group with 14 to 24 carbon atoms and one unsaturated bond or a hydrocarbon group with 14 to 24 carbon atoms and one unsaturated bond, with the peptide of the present invention bound thereto 0.2 to 80 mol %;
(IV) a liposome stabilizer 0.2 to 75 mol %.
(100 mol % in total)

As a more preferable mode of the phospholipid membrane constituting the liposome moiety of the peptide-bound liposome of the present invention, the following composition can be mentioned:
the above-described component (I) 2 to 80 mol %
the above-described component (II) 0.1 to 70 mol %
the above-described component (III) 0.3 to 60 mol %
the above-described component (IV) 10 to 70 mol %
(100 mol % in total)

As a still more preferable mode of the phospholipid membrane constituting the liposome moiety of the peptide-bound liposome of the present invention, the following composition can be mentioned:
the above-described component (I) 4 to 60 mol %
the above-described component (II) 0.1 to 60 mol %
the above-described component (III) 0.4 to 50 mol %
the above-described component (IV) 20 to 60 mol %
(100 mol % in total)

As a particularly preferable mode of the phospholipid membrane constituting the liposome moiety of the peptide-bound liposome of the present invention, the following composition can be mentioned:
the above-described component (I) 5 to 40 mol %
the above-described component (II) 0.1 to 50 mol %
the above-described component (III) 0.5 to 25 mol %
the above-described component (IV) 25 to 55 mol %
(100 mol % in total)

The peptide-bound liposome of the present invention is characterized in that the unsaturated acyl group or unsaturated hydrocarbon group contained in the phospholipid in the phospholipid membrane constituting the liposome moiety thereof has 14 to 24 carbon atoms; as far as the effect of the present invention is not interfered with, the phospholipid membrane may comprise a phospholipid comprising an unsaturated acyl group or unsaturated hydrocarbon group having a number of carbon atoms less than 14 or exceeding 24. The ratio of the number of unsaturated acyl groups or unsaturated hydrocarbon groups with 14 to 24 carbon atoms, relative to the total number of all unsaturated acyl groups or unsaturated hydrocarbon groups contained in the phospholipid in the phospholipid membrane constituting the liposome moiety of the peptide-bound liposome of the present invention is, for example, 50% or more, preferably 60% or more, more preferably 75% or more, still more preferably 90% or more, and most preferably 97% or more (for example, substantially 100%).

The phospholipid membrane constituting the liposome moiety of the peptide-bound liposome of the present invention may comprise, as far as the effect of the present invention is not interfered with, a lipid, other than a phospholipid, having an acyl group or hydrocarbon group with 14 to 24 carbon atoms. The content of the lipid is normally 40 mol % or less, preferably 20 mol % or less, more preferably 10 mol % or less, and still more preferably 5 mol % or less (for example, substantially 0 mol %).

The liposome moiety of the peptide-bound liposome of the present invention can be obtained by a method wherein components (phospholipid, reactive phospholipid, liposome stabilizer, and the peptide of the present invention and the like) are appropriately blend and processed, and the product is added to an appropriate solvent, or other methods.

For example, methods of production such as the extrusion method, vortex mixer method, sonication method, surfactant removal method, reversed-phase evaporation method, ethanol injection method, pre-vesicle method, French press method, W/O/W emulsion method, annealing method, and freeze-thaw method can be mentioned. The form of liposome is not particularly limited; by choosing one of the aforementioned methods of liposome production as appropriate, liposomes having various sizes and forms such as multilayer liposomes, small monolayer membrane liposomes, and large monolayer membrane liposomes can be produced.

The particle diameter of the liposome is not particularly limited, but in view of storage stability and the like, the particle diameter is 20 to 600 nm, preferably 30 to 500 nm, more preferably 40 to 400 nm, still more preferably 50 to 300 nm, and most preferably 70 to 230 nm.

In the present invention, to improve the physicochemical stability of the liposome, during or after preparing the liposome, a saccharide or a polyhydric alcohol may be added to the internal water phase and/or external water phase of the liposome. In particular, if long storage or storage during preparation making is required, it is preferable to add and dissolve a saccharide or polyhydric alcohol as a liposome protector, and to remove water by freeze-drying, to obtain a freeze-dried product of a phospholipid composition.

As examples of the saccharide, monosaccharides such as glucose, galactose, mannose, fructose, inositol, ribose, and xylose; disaccharides such as saccharose, lactose, cellobiose, trehalose, and maltose; trisaccharides such as raffinose and melezitose; oligosaccharides such as cyclodextrin; polysaccharides such as dextrin; sugar alcohols such as xylitol, sorbitol, mannitol, and maltitol, and the like can be mentioned. Of these saccharides, monosaccharides or disaccharides are preferable, and glucose or saccharose is particularly preferable in view of availability and the like.

As examples of the polyhydric alcohol, glycerin compounds such as glycerin, diglycerin, triglycerin, tetraglycerin, pentaglycerin, hexaglycerin, heptaglycerin, octaglycerin, nonaglycerin, decaglycerin, and polyglycerin; sugar alcohol compounds such as sorbitol and mannitol; ethylene glycol, diethylene glycol, triethylene glycol, tetraethylene glycol, pentaethylene glycol, hexaethylene glycol, heptaethylene glycol, octethylene glycol, nonethylene glycol and the like can be mentioned. Thereof, glycerin, diglycerin, triglycerin, sorbitol, mannitol, and polyethylene glycols having molecular weights of 400 to 10,000 are preferable in view of availability.

The concentration of the saccharide or polyhydric alcohol contained in the internal water phase and/or external water phase, based on concentration by weight relative to the liposome liquid, is, for example, 1 to 20% by weight, preferably 2 to 10% by weight.

When the peptide-bound liposome of the present invention is produced, it is possible to obtain the peptide-bound liposome of the present invention conveniently by preparing a liposome prior to the binding of the peptide of the present invention, then binding the peptide of the present invention.

For example, a suspension of a liposome comprising a phospholipid, a liposome stabilizer, and a reactive phospholipid for binding the peptide of the present invention to the membrane surface is prepared, and sucrose, one of the aforementioned saccharides, is added to the external water phase thereof at about 2 to 10% by weight, and dissolved. This saccharide-added preparation is transferred to a 10 ml glass vial, placed in a shelf rack type freeze-drier, and cooled to −40° C. and the like to freeze the sample, after which a freeze-dried product is obtained by a conventional method.

The freeze-dried product of the liposome obtained here can be stored for a long time because it is deprived of water; by adding the particular peptide of the present invention when necessary, and performing the subsequent steps, the completed peptide-bound liposome of the present invention can be obtained conveniently and quickly. If the interaction between the peptide of the present invention and the liposome is intense and the instability is severe and the like, it is very convenient to preserve the liposome at the stage of a freeze-dried product, as described here, and to bind the peptide of the present invention when necessary before use.

The phospholipid membrane constituting the liposome moiety of the peptide-bound liposome of the present invention can have a phospholipid with the peptide of the present invention bound thereto. As methods of obtaining a liposome comprising a phospholipid with the peptide of the present invention bound thereto, the following methods (A) and (B) can be mentioned.

(A) A method wherein a liposome comprising a phospholipid, a reactive lipid, and a liposome stabilizer is prepared, the peptide of the present invention and a divalent reactive compound are added thereto, and the functional group of the reactive phospholipid contained in the liposome and the functional group of the peptide of the present invention are joined via a divalent reactive compound. The divalent reactive compound used here can be the same as that used to prepare a terminal-modified derivative of the reactive phospholipid. Specifically, as divalent reactive compounds having an aldehyde group, glyoxal, glutaraldehyde, succindialdehyde, terephthalaldehyde and the like can be mentioned. Preferably, glutaraldehyde can be mentioned. Furthermore, as divalent reactive compounds having a succinic imide group, dithiobis(succinimidyl propionate), ethylene glycol-bis(succinimidyl succinate), disuccinimidyl succinate, disuccinimidyl suberate, or disuccinimidyl glutarate and the like can be mentioned. As divalent reactive compounds having a succinimide group at one end and a maleimide group at the other end, N-succinimidyl-4-(p-maleimidophenyl)butyrate, sulfosuccinimidyl-4-(p-maleimidophenyl)butyrate, N-succinimidyl-4-(p-maleimidophenyl)acetate, N-succinimidyl-4-(p-maleimidophenyl)propionate, succinimidyl-4-(N-maleimidethyl)-cyclohexane-1-carboxylate, sulfosuccinimidyl-4-(N-maleimidethyl)-cyclohexane-1-carboxylate, N-(γ-maleimidobutyryloxy)succinimide, N-(ε-maleimidocaproyloxy)succinimide and the like can be used. Using such a divalent reactive compound, a terminal-modified derivative of a reactive phospholipid (for example, phosphatidylethanolamine) having a maleimide group as a functional group is obtained.

(B) A method wherein a liposome comprising a phospholipid, a reactive phospholipid, and a liposome stabilizer is prepared, the peptide of the present invention is added thereto, and the functional group of the reactive phospholipid contained in the liposome and the functional group of the peptide of the present invention are joined and bound.

As examples of the kind of the bond in the foregoing (A) and (B), ionic bonds, hydrophobic bonds, covalent bonds and the like can be mentioned, and the bond is preferably a covalent bond. Furthermore, as specific examples of the covalent bond, a Schiff's base bond, an amide bond, a thioether bond, an ester bond and the like can be mentioned.

These two methods both enable the binding of the peptide of the present invention to the reactive phospholipid contained in the phospholipid membrane constituting the liposome, resulting in the formation of a phospholipid having the peptide of the present invention bound thereto in the liposome.

As a specific example of a method of binding the raw material liposome and the peptide of the present invention via a divalent reactive compound, in the aforementioned method (A), a method with the use of a Schiff's base bond can be mentioned. As a method of binding a liposome and the peptide of the present invention via a Schiff's base bond, a method can be mentioned wherein a liposome having an amino group on the surface thereof is prepared, the peptide of the present invention is added to a suspension of the liposome, then a dialdehyde is added as a divalent reactive compound, and the amino group on the liposome surface and the amino group in the peptide of the present invention are bound via a Schiff's base.

As a specific example of this binding procedure, the following method can be mentioned.

(A-1) To obtain a liposome having an amino group on the surface thereof, a reactive phospholipid having an acyl group with 14 to 24 carbon atoms and one unsaturated bond or a hydrocarbon group with 14 to 24 carbon atoms and one unsaturated bond (e.g., phosphatidylethanolamine) is mixed in a liposome raw material lipid (phospholipid, liposome stabilizer and the like) to prepare a liposome wherein a specified amount of amino groups is present on the liposome surface.

(A-2) The peptide of the present invention is added to the liposome suspension.

(A-3) Next, glutaraldehyde, as a divalent reactive compound, is added, and the reaction is allowed to proceed for a specified time to form a Schiff's base bond between the liposome and the peptide of the present invention.

(A-4) Thereafter, to inactivate the reactivity of excess glutaraldehyde, glycine, as a water-soluble compound containing an amino group, is added to the liposome suspension to cause the reaction.

(A-5) The portion of the peptide of the present invention not bound to the liposome, the reaction product of glutaraldehyde and glycine, and excess glycine are removed by a method such as gel filtration, dialysis, ultrafiltration or centrifugation, to yield a suspension of the peptide-bound liposome of the present invention.

As a specific example of the method (B) above, a method can be mentioned wherein a reactive phospholipid having a functional group capable of forming an amide bond, a thioether bond, a Schiff's base bond, an ester bond and the like is introduced into the phospholipid membrane constituting the liposome. As specific examples of the functional group, a succinimide group, a maleimide group, an amino group, an imino group, a carboxyl group, a hydroxy group, a thiol group and the like can be mentioned.

As an example of the reactive phospholipid to be introduced into the phospholipid membrane constituting the liposome, the aforementioned terminal-modified derivative of a reactive phospholipid, modified at the amino group end thereof, having an acyl group with 14 to 24 carbon atoms and one unsaturated bond or a hydrocarbon group with 14 to 24 carbon atoms and one unsaturated bond (e.g., phosphatidylethanolamine) can be used.

Specific examples of this binding procedure are hereinafter described with reference to a case wherein diacylphosphatidylethanolamine is used.

(B-1) A diacylphosphatidylethanolamine having an acyl group with 14 to 24 carbon atoms and one unsaturated bond and disuccinimidyl succinate are reacted only at one end by a known method to yield a disuccinimidyl succinate-bound diacylphosphatidylethanolamine having a succinimide group as a functional group at the end.

(B-2) The aforementioned disuccinimidyl succinate-bound diacylphosphatidylethanolamine and other liposome components (phospholipid, liposome stabilizer and the like) are mixed by a publicly known method to prepare a liposome having a succinimide group as a functional group on the surface thereof.

(B-3) The peptide of the present invention is added to the aforementioned liposome suspension to allow the amino group in the peptide of the present invention and the succinimide group on the liposome surface to react with each other.

(B-4) The unreacted portion of the peptide of the present invention, reaction byproducts and the like are removed by a method such as gel filtration, dialysis, ultrafiltration or centrifugation to yield a suspension of a liposome comprising a phospholipid with the peptide of the present invention bound thereto.

When the liposome and the peptide of the present invention are bound, it is practically preferable that an amino group or a thiol group, which are often contained as a functional group, be the subject. When an amino group is the subject, a Schiff's base bond can be formed by reacting with a succinimide group. When a thiol group is the subject, a thioether bond can be formed by reacting with a maleimide group.

Using the peptide or peptide-bound liposome of the present invention, it is possible to potently induce cytotoxic T lymphocytes (CTL) that recognize the peptide of the present invention (preferably the epitope peptide of the present invention) in an HLA (preferably HLA-A*0201 or HLA-A*2402)-restricted and specific manner. The cytotoxic T lymphocytes induced by the peptide or peptide-bound liposome of the present invention kill the cells presenting the peptide of the present invention onto HLA as a result of infection with avian influenza virus, and eliminate these cells. Therefore, the peptide and peptide-bound liposome of the present invention are useful as a cytotoxic T lymphocyte activator or avian influenza virus vaccine.

As described above, the peptide of the present invention comprises an epitope highly conserved in drift mutants and shift mutants of avian influenza virus. Therefore, the peptide and peptide-bound liposome of the present invention are useful as vaccines for a wide variety of types [(H1 to H16)×(N1 to N9)] of avian influenza viruses, and are particularly effective against highly pathogenic avian influenza virus (type H5N1). The peptide and peptide-bound liposome of the present invention are also useful as vaccines for various mutants.

When the peptide or peptide-bound liposome of the present invention is used as a cytotoxic T lymphocyte activator or avian influenza virus vaccine, it can be prepared as a preparation according to a conventional method. The peptide or peptide-bound liposome of the present invention is of low toxicity, and can be administered orally or parenterally (e.g., intravascular administration, subcutaneous administration and the like) as a liquid as is, or as a pharmaceutical composition in an appropriate dosage form, to humans, non-human mammals (e.g., rats, rabbits, sheep, pigs, cattle, cats, dogs, monkeys and the like), birds (chicken, geese, domestic ducks, ostriches, quails and the like). The animal being the subject of administration of the peptide or peptide-bound liposome of the present invention is normally a mammal or bird which can be infected with the target avian influenza virus. The peptide or peptide-bound liposome of the present invention is normally administered parenterally.

The cytotoxic T lymphocyte activator and avian influenza virus vaccine of the present invention may be administered as an active ingredient peptide or peptide-bound liposome as it is, or may be administered as an appropriate pharmaceutical composition. The pharmaceutical composition used for the administration may comprise the above-described peptide or peptide-bound liposome and a pharmacologically acceptable carrier, diluent or excipient. Such a pharmaceutical composition is provided as a dosage form suitable for oral or parenteral administration.

As examples of the composition for parenteral administration, injections, suppositories and the like are used; the injections may include dosage forms such as intravenous injections, subcutaneous injections, intracutaneous injections, intramuscular injections, and drip infusion injections. Such an injection can be prepared according to a known method. The injection can be prepared by, for example, dissolving or suspending the above-described peptide or peptide-bound liposome in a sterile aqueous solvent normally used for injections. As examples of the aqueous solvent for injection, distilled water; physiological saline; buffer solutions such as phosphate buffer solution, carbonate buffer solution, tris buffer solution, and acetate buffer solution, and the like can be used. The pH of the aqueous solvent is 5 to 10, preferably 6 to 8. The prepared injection liquid is preferably filled in an appropriate ampoule.

Also, by subjecting a solution of the peptide of the present invention or a suspension of the peptide-bound liposome of the present invention to a treatment such as vacuum drying or freeze-drying, a powder preparation of the peptide of the present invention or the peptide-bound liposome of the present invention can also be prepared. The peptide of the present invention or the peptide-bound liposome of the present invention can be preserved in a powder state, and can be supplied for use by dispersing the powder in an aqueous solvent for injection freshly before use.

The cytotoxic T lymphocyte activator and avian influenza virus vaccine of the present invention, to enhance the effect thereof, may further comprise an adjuvant. As the adjuvant, aluminum hydroxide gel, Freund's complete adjuvant, Freund's incomplete adjuvant, *Bordetella pertussis* adjuvant, poly (I,C), CpG-DNA and the like can be mentioned, and CpG-DNA is particularly preferable. CpG-DNA, a DNA comprising the bacterial non-methylated CpG motif, is known to work as a ligand for a particular receptor (Toll-like receptor 9) (for details, see Biochim. Biophys. Acta 1489, 107-116 (1999) and Curr. Opin. Microbiol. 6, 472-477 (2003)). CpG-DNA is capable of enhancing the induction of cytotoxic T lymphocytes by the peptide or peptide-bound liposome of the present invention, by activating dendritic cells (DC).

The content of an active ingredient (the peptide or peptide-bound liposome of the present invention) in the pharmaceutical composition is normally about 0.1 to 100% by weight, preferably about 1 to 99% by weight, and still more preferably about 10 to 90% by weight, relative to the entire pharmaceutical composition.

If the cytotoxic T lymphocyte activator or avian influenza virus vaccine of the present invention comprises an adjuvant, the content of the adjuvant (for example, CpG-DNA) can be set as appropriate, as far as the induction of cytotoxic T lymphocytes can be enhanced, and the content is normally about 0.01 to 10% by weight, preferably about 0.1 to 5% by weight, relative to the entire pharmaceutical composition.

The dose of the peptide of the present invention or the peptide-bound liposome of the present invention varies depending on the subject of administration, method of administration, dosage form and the like; for example, in the case of activation of cytotoxic T lymphocytes in a living organism by subcutaneous administration or nasal administration, the dose is given normally in the range of 1 μg to 1000 μg, preferably 20 μg to 100 μg, based on the peptide of the present invention, per administration, for each adult (weighing 60 kg), normally for 4 weeks to 18 months, 2 to 3 times. In the case of prevention of avian influenza virus infections by subcutaneous administration, the dose is given normally in the range of 1 μg to 1000 μg, preferably 20 μg to 100 μg, based on the peptide of the present invention, per administration, normally for 4 weeks to 18 months, 2 times to 3 times.

EXAMPLES

The present invention is hereinafter described in more detail with reference to the following examples, to which, however, the present invention is not limited by any means.

Example 1

Search for CTL Epitopes

Out of the amino acid sequences of 8 kinds of viral internal proteins (M1, M2, NP, NS1, NS2, PA, PB1, PB2) of the highly pathogenic avian influenza virus A/Hong_Kong/483/97 (H5N1) strain, epitopes expected to bind to HLA-A*0201 or HLA-A*2402, a human major histocompatibility antigen complex (MHC) class I molecule, to exhibit antigenicity against killer T cells (CTL) were searched for, using the following 4 kinds of estimation programs available on the Internet.

a. NetCTL server 1.2 (www.cbs.dtu.dk/services/NetCTL/)
b. nHLAPred (www.imtech.res.in/raghava/nhlapred/)
c. BIMAS (www-bimas.cit.nih.gov/molbio/hla_bind/)
d. SYFPEITHI (www.syfpeithi.de/home.htm)

Out of the 41 kinds of candidate peptides expected by each program to exhibit epitope activity,

```
                                  (SEQ ID NO: 1)
PB1_410:      GMFNMLSTV (SEQ ID NO: 2)
PA_130:       YYLEKANKI, (SEQ ID NO: 3)
PA_262:       KTTPRPLRL, (SEQ ID NO: 4)
PB1_430:      RYTKTTYWW, (SEQ ID NO: 5)
PB1_482:      SYINRTGTF, (SEQ ID NO: 6)
PB1_688:      MYQKCCTLF,
```

-continued

```
                                  (SEQ ID NO: 7)
PB2_549:      TYQWIIRNW, (SEQ ID NO: 8)
PB2_322:      SFSFGGFTF, (SEQ ID NO: 9)
PB1_216:      SYLIRALTL, (SEQ ID NO: 16)
M2_40:        LWILDRLFF, (SEQ ID NO: 17)
PB2_117:      TYFEKVERL, (SEQ ID NO: 18)
PB1_331:      EWFRNVLSI, (SEQ ID NO: 19)
PA_8:         CFNPMIVEL, (SEQ ID NO: 20)
NP_257:       IFLARSALI, (SEQ ID NO: 21)
NP_481:       MSNEGSYFF, (SEQ ID NO: 22)
M2_2:         SLLTEVETL
``` were selected; after peptides were synthesized, the CTL activity induced by immunization with each peptide was measured.

Example 2

Preparation of Liposome

1) Preparation of Mixed Lipid Powder

Synthesis of a reactive phospholipid consisting of terminal-modified phosphatidylethanolamine (succinimidyl group-dioleoylphosphatidylethanolamine)

2 g of dioleoylphosphatidylethanolamine and 180 μl of triethylamine were added to, and dissolved in, 50 ml of chloroform, and this solution was placed in a 300-ml capacity four-mouthed flask. While stirring this flask with a magnetic stirrer at room temperature, a separately prepared solution of 3 g of disuccinimidyl suberate being a divalent reactive compound in 80 ml of chloroform was added drop by drop over 4 hours according to a conventional method, to allow one end of the disuccinimidyl suberate to react to the amino group of the dioleoylphosphatidylethanolamine. This crude reaction solution was transferred to an eggplant type flask, and the solvent was distilled off using an evaporator. Next, a small amount of chloroform sufficient to dissolve the crude reaction product was added to this flask to obtain a high-concentration crude reaction product solution, and column chromatography was performed using a silica gel, previously equilibrated with chloroform/methanol/water (65/25/1, ratio by volume), according to a conventional method; only the desired fraction wherein one end of the disuccinimidyl suberate is bound to the amino group of the dioleoylphosphatidylethanolamine was recovered, and the solvent was distilled off to yield succinimide group-dioleoylphosphatidylethanolamine being the desired reactive phospholipid.

2) Preparation of Mixed Lipid Powder 1.3354 g (1.6987 mmol) of dioleoylphosphatidylcholine, 0.2886 g (0.2831 mmol) of the succinimide group-dioleoylphosphatidylethanolamine prepared in the foregoing section, 0.7663 g (1.9818 mmol) of cholesterol and 0.4513 g (0.5662 mmol) of sodium dioleoylphosphatidylglycerol were taken in an eggplant type flask, 50 ml of a mixed solvent of chloroform/methanol/water (65/25/4, ratio by volume) was placed therein, and the contents were dissolved at 40° C. Next, the solvent was distilled off under reduced pressure using a rotary evaporator to yield a lipid film. Furthermore, 30 ml of distilled water for injection was added, and this was followed by stirring to yield a homogeneous slurry. This slurry was frozen, and dried in a freeze-drier for 24 hours to yield a mixed lipid powder.

3) Preparation of Liposome

Next, 60 ml of a separately prepared buffer solution (1.0 mM $Na_2HPO_4/KH_2PO_4$, 0.25M saccharose, pH 7.4, hereinafter abbreviated as buffer solution) was placed in an eggplant type flask containing the above-described mixed lipid powder, and the lipid was hydrated with stirring at 40° C., to yield a liposome. Next, using an extruder, the particle diameter of the liposome was adjusted. First, the liposome was passed through an 8 μm polycarbonate filter, and subsequently through 5 μm, 3 μm, 1 μm, 0.65 μm, 0.4 μm and 0.2 μm filters in this order. Liposome particles having a mean particle diameter of 206 nm (measured by the dynamic light scattering method) were obtained.

Example 3

Preparation of Liposome Preparation 1.5 ml of the liposome of Example 2 (Preparation of liposome) was taken in a test tube, 3 ml of a separately prepared solution of each peptide (1.25 mM, solution of a buffer solution) was added, and thereafter the solution was gently stirred at 5° C. for 48 hours to allow the reaction. This reaction liquid was subjected to gel filtration by a conventional method using Sepharose CL-4B, previously equilibrated with the buffer solution. Because the liposome fraction is turbid in white, the desired fraction is easily identifiable, but a UV detector and the like may be used for the identification.

The phosphorus concentration in the liposome suspension thus obtained was measured (Phospholipid Test Wako), and the phosphorus concentration derived from the phospholipid was adjusted to 2 mM by diluting the suspension with the buffer solution to yield a suspension of each peptide-bound liposome.

Example 4

Detection of CTL Activity

Detection of peptide activity, with an emphasis on the potential for inducing killing activity in vivo, was performed by the method described below. First, mice that do not have MHC class I molecules indigenous to mice (H2-D and H2-K) and express the HLA-A*0201 molecule (HHD mice) for the peptide of SEQ ID NO:1, and transgenic mice that do not have MHC class I molecules indigenous to mice (H2-D and H2-K) and express the HLA-A*2402 molecule (A24Tg) for the peptides of SEQ ID NO:2 and beyond, were twice immunized at a 1-week interval with each candidate peptide bound to an oleic acid liposome (0.5 μg/μl administered at 200 μl/animal) and CpG5002 (5'-TCCATGACGTTCTGATGTT-3' (SEQ ID NO:23); for details, see Vaccine 25, 4914-4921 (2007)) (10 μ/animal). Six days after final immunization, target cells (A24Tg mouse splenocytes $5\times10^5$ cells/animal) labeled with the immunizing peptide (0.5 μM) and a fluorescent dye (CFDA-SE), along with control, were intravenously administered; 16 hours later, the animals were euthanized, thereafter the spleens were recovered, and the percent reduction of target cells therein was analyzed using a flow cytometer.

Preparation of Spleen-Adherent Cells (SAC) and CD4+ and CD8+ T Cells

A splenocyte suspension was prepared using RPMI-1640 containing 10% FCS. Cells ($5\times10^7$ cells) in 5 ml of a culture medium containing 10% FCS were plated on a 50 mm plastic tissue culture dish (No.#3002; BectonDickinson Labware, Franklin Lakes, N.J.), and incubated in a moisturized 5% $CO_2$ atmosphere at 37° C. for 2 hours. After the cultivation, non-adhering cells were removed by gentle washing in a warm medium, then adhering cells were recovered using a cell scraper. Purification of CD4+ and CD8+ T cells from splenocytes (SC) of mice immunized with each peptide-alum was performed by means of the magnetic cell sorter system MACS, as directed in the manufacturer's protocol, using anti-CD4 and anti-CD8 antibody-coated microbeads (Miltenyi Biotec GmbH). The T cells were suspended in RPMI-1640 containing 10% FCS at a cell density of $2\times10^6$ ml.

In vivo Cytotoxicity Assay (Measurement of CTL Activity)

The above-described mouse splenocytes were labeled with 0.5 or 5 μM CFDA-SE (Sigma) at room temperature for 15 minutes, and twice washed. Next, the cells with bright CFDA-SE (M2) were pulsed with 0.5 μg/ml of each peptide at 37° C. for 90 minutes. The cells with dark CFDA-SE (M1), as controls, were pulsed with irrelevant NP366-374 (ASNENMDAM) peptide at 37° C. for 90 minutes. The cells were mixed in a 1:1 ratio; a total of $5\times10^6$ cells were intravenously injected into mice that had received an injection of 100 μg of anti-IL-10 monoclonal antibody 2A5, 5 μg of CpG5002 and each peptide-bound liposome 1 to 2 weeks previously. After 8 hours, the splenocytes were recovered from each mouse and analyzed by flow cytometry. The degree of reduction in the fluorescence-labeled splenocytes of the fraction pulsed with each peptide served as an index of CTL activity. If CTL is induced in the mice immunized with each peptide-bound liposome, only the fluorescence-labeled splenocytes of the fraction pulsed with each peptide disappear.

Results

The peptides that exhibited some activity and results of screening thereof are shown below.

TABLE 1

| Name of peptide | Amino acid sequence | | Specific killing |
|---|---|---|---|
| PB1_410 | GMFNMLSTV | (SEQ ID NO: 1) | 87% |
| PA_130 | YYLEKANKI | (SEQ ID NO: 2) | 95% |
| PA_262 | KTTPRPLRL | (SEQ ID NO: 3) | 58% |
| PB1_430 | RYTKTTYWW | (SEQ ID NO: 4) | 96% |
| PB1_482 | SYINRTGTF | (SEQ ID NO: 5) | 56% |
| PB1_688 | MYQKCCTLF | (SEQ ID NO: 6) | 89% |
| PB2_549 | TYQWIIRNW | (SEQ ID NO: 7) | 96% |
| PB2_322 | SFSFGGFTF | (SEQ ID NO: 8) | 38% |
| PB1_216 | SYLIRALTL | (SEQ ID NO: 9) | 22% |
| M2_40 | LWILDRLFF | (SEQ ID NO: 16) | 10% |
| PB2_117 | TYFEKVERL | (SEQ ID NO: 17) | 13% |
| PB1_331 | EWFRNVLSI | (SEQ ID NO: 18) | 7% |
| PA_8 | CFNPMIVEL | (SEQ ID NO: 19) | 10% |
| NP_257 | IFLARSALI | (SEQ ID NO: 20) | 16% |

TABLE 1-continued

| Name of peptide | Amino acid sequence | Specific killing |
|---|---|---|
| NP_481 | MSNEGSYFF (SEQ ID NO: 21) | 5% |
| M2_2 | SLLTEVETL (SEQ ID NO: 22) | — |

Of the peptides selected by the search, PB1_410: GMFNMLSTV (SEQ ID NO:1), PA_130: YYLEKANKI (SEQ ID NO:2), PA_262: KTTPRPLRL (SEQ ID NO:3), PB1_430: RYTKTTYWW (SEQ ID NO:4), PB1_482: SYINRTGTF (SEQ ID NO:5), PB1_688: MYQKCCTLF (SEQ ID NO:6), PB2_549: TYQWIIRNW (SEQ ID NO:7), PB2_322: SFSFGGFTF (SEQ ID NO:8), and PB1_216: SYLIRALTL (SEQ ID NO:9) exhibited high CTL activity, whereas M2_40: LWILDRLFF (SEQ ID NO:16), PB2_117: TYFEKVERL (SEQ ID NO:17), PB1_331: EWFRNVLSI (SEQ ID NO:18), PA_8: CFNPMIVEL (SEQ ID NO:19), NP_257: IFLARSALI (SEQ ID NO:20), NP_481: MSNEGSYFF (SEQ ID NO:21), and M2_2: SLLTEVETL (SEQ ID NO:22) exhibited low activity.

INDUSTRIAL APPLICABILITY

According to the present invention, it is possible to provide a highly effective vaccine for highly pathogenic avian influenza virus, which is likely to cause pandemics, the vaccine being unlikely to be influenced by mutations of the surface protein thereof. According to the avian influenza vaccine of the present invention, it is possible to provide a novel pre-pandemic vaccine that overcomes the drawback of currently available pre-pandemic vaccines that their effect is limited if the actually prevalent strain (type/subtype) is different from the expected one.

What is claimed is:

1. An immunogenic composition comprising a peptide-bound liposome and a pharmaceutically acceptable carrier, wherein the peptide-bound liposome comprises:
   (a) a phospholipid comprising (i) an acyl group with 14 to 24 carbon atoms and one unsaturated bond or a hydrocarbon group with 14 to 24 carbon atoms and one unsaturated bond, and (ii) a liposome stabilizer, and
   (b) a peptide bound to the surface of the liposome, wherein the peptide consists of SEQ ID NO: 7.

2. The immunogenic composition of claim 1, further comprising CpG-DNA.

3. An avian influenza virus vaccine comprising a peptide-bound liposome comprising:
   (a) a phospholipid comprising (i) an acyl group with 14 to 24 carbon atoms and one unsaturated bond or a hydrocarbon group with 14 to 24 carbon atoms and one unsaturated bond, and (ii) a liposome stabilizer, and
   (b) a peptide bound to the surface of the liposome, wherein the peptide consists of SEQ ID NO: 7.

4. The avian influenza virus vaccine of claim 3, further comprising CpG-DNA.

5. A method of activating cytotoxic T lymphocytes in a mammal, comprising administering to the mammal a peptide-bound liposome comprising:
   (a) a phospholipid comprising (i) an acyl group with 14 to 24 carbon atoms and one unsaturated bond or a hydrocarbon group with 14 to 24 carbon atoms and one unsaturated bond, and (ii) a liposome stabilizer, and
   (b) a peptide bound to the surface of the liposome, wherein the peptide consists of SEQ ID NO: 7.

6. The method of claim 5, further comprising administering CpG-DNA.

7. A method of vaccinating a mammal against avian influenza virus, comprising administering to the mammal a peptide-bound liposome comprising:

(a) a phospholipid comprising (i) an acyl group with 14 to 24 carbon atoms and one unsaturated bond or a hydrocarbon group with 14 to 24 carbon atoms and one unsaturated bond, and (ii) a liposome stabilizer, and (b) a peptide bound to the surface of the liposome, wherein the peptide consists of SEQ ID NO: 7.

8. The method of claim 7, further comprising administering CpG-DNA.

9. A peptide-bound liposome comprising:

(a) a phospholipid comprising (i) an acyl group with 14 to 24 carbon atoms and one unsaturated bond or a hydrocarbon group with 14 to 24 carbon atoms and one unsaturated bond, and (ii) a liposome stabilizer, and (b) a peptide bound to the surface of the liposome, wherein the peptide consists of SEQ ID NO: 7.

10. The peptide-bound liposome of claim 9, wherein the HLA of the peptide is HLA-A*0201 or HLA-A*2402.

11. The peptide-bound liposome of claim 9, wherein the phospholipid is a phospholipid having an acyl group with 14 to 24 carbon atoms and one unsaturated bond.

12. The peptide-bound liposome of claim 9, wherein the acyl group is an oleoyl group.

13. The peptide-bound liposome of claim 9, wherein the phospholipid is at least one selected from among diacylphosphatidylserine, diacylphosphatidylglycerol, diacylphosphatidic acid, diacylphosphatidylcholine, diacylphosphatidylethanolamine, succinimidyl-diacylphosphatidylethanolamine, and maleimido-diacylphosphatidylethanolamine.

14. The peptide-bound liposome of claim 9, wherein the liposome stabilizer is cholesterol.

15. The peptide-bound liposome of claim 9, wherein the peptide is bound to a phospholipid contained in a phospholipid membrane constituting the liposome, wherein the phospholipid has an acyl group with 14 to 24 carbon atoms and one unsaturated bond or a hydrocarbon group with 14 to 24 carbon atoms and one unsaturated bond.

16. The peptide-bound liposome of claim 9, wherein the liposome has the following composition:

(i) 1 to 99.8 mol % of a phospholipid having an acyl group with 14 to 24 carbon atoms and one unsaturated bond or a hydrocarbon group with 14 to 24 carbon atoms and one unsaturated bond, and (ii) 0.2 to 75 mol % of a liposome stabilizer.

17. The peptide-bound liposome of claim 9, wherein the liposome has the following composition:

(i) 1 to 85 mol % of an acidic phospholipid having an acyl group with 14 to 24 carbon atoms and one unsaturated bond or a hydrocarbon group with 14 to 24 carbon atoms and one unsaturated bond, (ii) 0.01 to 80 mol % of a neutral phospholipid having an acyl group with 14 to 24 carbon atoms and one unsaturated bond or a hydrocarbon group with 14 to 24 carbon atoms and one unsaturated bond, (iii) 0.2 to 80 mol % of a phospholipid having an acyl group with 14 to 24 carbon atoms and one unsaturated bond or a hydrocarbon group with 14 to 24 carbon atoms and one unsaturated bond with a peptide bound thereto, and (iv) 0.2 to 75 mol % of a liposome stabilizer.

* * * * *